United States Patent
Asai et al.

(10) Patent No.: US 7,204,977 B2
(45) Date of Patent: Apr. 17, 2007

(54) POWDER-CONTAINING OIL-IN-WATER EMULSIFIED COMPOSITION

(75) Inventors: Ayumi Asai, Yokohama (JP); Yoshimasa Miura, Yokohama (JP); Satoshi Tomomasa, Yokohama (JP)

(73) Assignee: Shiseido Co., Ltd., Tokyo (JP)

(*) Notice: Subject to any disclaimer, the term of this patent is extended or adjusted under 35 U.S.C. 154(b) by 0 days.

(21) Appl. No.: 10/521,019

(22) PCT Filed: Jul. 15, 2003

(86) PCT No.: PCT/JP03/08962

§ 371 (c)(1),
(2), (4) Date: Jan. 12, 2005

(87) PCT Pub. No.: WO2004/006871

PCT Pub. Date: Jan. 22, 2004

(65) Prior Publication Data

US 2005/0228056 A1    Oct. 13, 2005

(30) Foreign Application Priority Data

Jul. 16, 2002    (JP) .............................. 2002-206448

(51) Int. Cl.
*A61Q 5/00* (2006.01)

(52) U.S. Cl. ...................... 424/70.12; 424/63; 424/64; 424/59; 516/31; 516/34; 516/33; 516/55

(58) Field of Classification Search ............. 424/70.12, 424/63, 64, 59; 516/31, 34, 33, 55
See application file for complete search history.

(56) References Cited

U.S. PATENT DOCUMENTS

| | | | | | |
|---|---|---|---|---|---|
| 4,122,029 | A | * | 10/1978 | Gee et al. ....................... 516/23 |
| 5,066,485 | A | * | 11/1991 | Brieva et al. .................. 424/63 |
| 5,651,793 | A | * | 7/1997 | Hoeffkes et al. ............... 8/406 |
| 5,929,163 | A | * | 7/1999 | Harashima ................... 524/837 |
| 6,096,325 | A | * | 8/2000 | Date et al. ................... 424/401 |
| 6,511,655 | B1 | * | 1/2003 | Muller et al. .................. 424/59 |

FOREIGN PATENT DOCUMENTS

| | | |
|---|---|---|
| EP | 1 093 794 A1 | 4/2001 |
| JP | 05-311076 | 11/1993 |
| JP | 07-112915 | 5/1995 |
| JP | 09-143023 | 6/1997 |
| JP | 09-143031 | 6/1997 |
| JP | 2001-158713 | 6/2001 |

* cited by examiner

*Primary Examiner*—Margaret G. Moore
(74) *Attorney, Agent, or Firm*—Snider & Associates; Ronald R. Snider

(57) ABSTRACT

There is provided an oil-in-water emulsified composition comprising hydrophobic powder particles, a polyether-modified silicone represented by formula (1), and an ionic water-soluble polymer compound, whereby the succulent feel originating from thickening effect rendered by the ionic water-soluble polymer compound and the effects intrinsic to the hydrophobic powder particles can be demonstrated stably over time in an oil-in-water emulsified composition obtained using an ionic water-soluble polymer compound, to which composition the powder particles are added.

9 Claims, No Drawings

POWDER-CONTAINING OIL-IN-WATER EMULSIFIED COMPOSITION

TECHNICAL FIELD

The present invention relates to an oil-in-water emulsified composition suitable for use as a cosmetic or other composition for external use.

BACKGROUND ART

Carboxyvinyl polymers or alkyl modified carboxyvinyl polymers and other ionic water-soluble polymer compounds produce increased viscosity by repulsion between ions, so it is possible to obtain high viscosity using even a small quantity thereof. It is therefore possible by using an ionic water-soluble polymer compound as a thickening agent to set a wide range of viscosities while minimizing the stickiness or slipperiness that is specific to a polymer, and also to impart a succulent and fresh feel to the consumer by using the thixotropy specific to the ionic water-soluble polymer compounds.

Ionic water-soluble polymer compounds are therefore widely used as a cosmetic starting material; particularly, as a water-phase thickening agent for water-based cosmetics, oil-in-water emulsified cosmetics, and the like.

Whereas an ionic water-soluble polymer compound has excellent characteristics as a thickening agent, cases are also identified in which it is difficult to appropriately control the viscosity of an added composition because of interaction due to contact with ionic groups of other ingredients or other ionic substances.

For example, because the surfaces of particles of titanium oxide powder generally used as a pigment are usually modified with alumina, zinc oxide, or the like, when the powder is added to a water phase that has been thickened with an ionic water-soluble polymer compound, ions derived from the modifying agent interact with the ionic water-soluble polymer compound, whereby general or localized reductions or increases in viscosity occur, the powder particles aggregate, and other effects are encountered, and it is difficult to provide a succulent feel from the natural thickening effect produced by the ionic water-soluble polymer compound and to obtain the effects produced by the titanium oxide powder while maintaining the stability of the composition.

In order to overcome these drawbacks, attempts have been made to control the interaction between ions by performing fluorine treatment or another hydrophobization treatment on titanium oxide or other powder particles (for example, see Japanese Laid-open Patent Application No. 9-143023, 7-112915, or 9-143031), but even when hydrophobized powder particles are dispersed in an oil phase in the process of manufacturing an oil-in-water emulsified composition, elution of ions into the water phase over time cannot be completely minimized, so it has been difficult to obtain a composition having adequately good stability.

Polysaccharides or derivatives thereof, for example, are also used as water-soluble polymer compounds that are not affected by ions originating from the added substance, but the added quantity thereof must be increased in order for a certain degree of viscosity to be retained by these water-soluble polymer compounds. Therefore, when only a small quantity of the polysaccharide or the like is used, the composition being added to is limited to an extremely low viscosity, and when a large quantity of the polysaccharide or the like is admixed therein in order to obtain a high viscosity, slipperiness, stickiness, and also runniness of the polymer and other effects occur, and it is difficult to provide an additive-containing composition having good tactile properties.

An object of the present invention is to provide a means for demonstrating a succulent feel originating from the increased viscosity induced by the ionic water-soluble polymer compound, and the effects intrinsic to the powder particles with stability over time, in an oil-in-water emulsified composition that uses an ionic water-soluble polymer compound, to which composition the powder particles are added.

DISCLOSURE OF THE INVENTION

The inventors carried out repeated investigations in order to overcome the foregoing drawbacks. As a result, they developed the present invention upon discovering that by forming an oil-in-water emulsion using a specific polyether-modified silicone as well as using hydrophobic powder particles as powder particles to be added, it is possible to secure the hydrophobic powder particles, including the eluted component thereof, in the oil phase for a long time, and to provide the desired oil-in-water emulsified composition.

Specifically, the present invention provides an oil-in-water emulsified composition (hereinafter referred to as "the emulsified composition") containing:

(a) hydrophobic powder particles;
(b) a polyether-modified silicone represented by the formula (I) below; and
(c) an ionic water-soluble polymer compound.

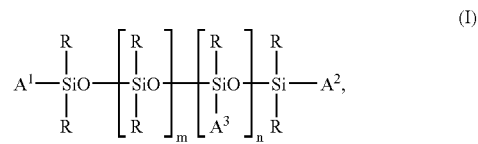

in which $A^1$, $A^2$, and n number of $A^3$'s are the same or different, and are a methyl group, a phenyl group, or a polyoxyalkylene group represented by the general formula:

wherein R' is a hydrogen atom, an acyl group, or an alkyl group with a carbon number of 1 to 4; and a and b are the same or different integers from 5 to 50; and at least one among $A^1$, $A^2$, and n number of $A^3$'s per molecule of the polyether-modified silicone(I) is the aforementioned polyoxyalkylene group;

R is a methyl group or a phenyl group;
m is an integer from 200 to 600; and
n is an integer from 1 to 40.

The emulsified composition preferably also contains (d) silicone oil.

BEST-MODE FOR CARRYING OUT THE INVENTION

Embodiments of the present invention will be described hereinafter.

(a) Hydrophobic Powder Particles
The hydrophobic powder particles containing the emulsified composition are powder particles having little interaction with water and little compatibility with water, and are usually lipophilic powder particles. The hydrophobic powder particles may be powder particles of a naturally hydrophobic material, and examples thereof include zinc stearate, aluminum stearate, calcium stearate, zinc myristate, or another metallic soap powder. The hydrophobic powder particles may also be powder particles obtained by using hydrophilic or hydrophobic powder particles as a base material and rendering this material hydrophobic.

Examples of such base materials include titanium oxide, iron oxide, magnesium oxide, zinc oxide, calcium oxide, calcium phosphate, calcium carbonate, alumina, aluminum hydroxide, barium sulfate, iridescent pigments (titanated mica, bismuth oxychloride, and the like), talc, and the like. Composite powder particles of powder particles that use these materials, or composite powder particles of these powder particles with nylon particles, polyethylene powder, polymethyl methacrylate (PMMA), silica, silicone resin, crystal cellulose, and other powders may be used in the present invention. These composite powder particles may be added in an unmodified state to the emulsified composition when the particles are inherently hydrophobic, or they may be hydrophobized as is the case with single-material hydrophilic powder particles and added to the emulsified composition when the particles are inherently hydrophilic.

Examples of the hydrophobization treatment performed on the powder particles as a base material include silicone treatment (treatment with methylhydrogen polysiloxane, dimethyl polysiloxane, methylphenyl polysiloxane, and other silicone oils; methyl trimethoxysilane, ethyl trimethoxysilane, hexyl trimethoxysilane, octyl trimethoxysilane, and other alkyl silanes; trifluoromethyl ethyl trimethoxy silane, heptadecafluorodecyl trimethoxysilane, and other fluoroalkyl silanes; and the like), fatty acid treatment (treatment with palmitic acid, isostearic acid, stearic acid, lauric acid, myristic acid, behenic acid, oleic acid, rosin acid, 12-hydroxystearic acid, and the like), fatty acid soap treatment (treatment with aluminum stearate, calcium stearate, 12-hydroxystearic acid, and the like), fatty acid ester treatment (treatment with a dextrin fatty acid ester, a cholesterol fatty acid ester, a sucrose fatty acid ester, a starch fatty acid ester, or the like), and the like. These hydrophobization treatments may be performed according to the usual method. Silicone treatment is suitable among these hydrophobization treatments for its ability to impart high stability to the powder particles, and for other effects thereof.

The shape or size of the hydrophobic powder particles is not particularly limited, and a spherical, tabular, petaled, or other shape may be employed. A suitable embodiment is one in which spherical particles are selected to allow the powder to be used as an external composition that utilizes reflected light to create a wrinkle hiding effect or chapping relief. In this case, it is possible by including the anti-wrinkle agent or anti-chapping agent described hereinafter in the emulsified composition to obtain a composition capable of producing an immediate wrinkle hiding effect or chapping relief, and long-term reduction of wrinkling and chapping. Furthermore, when spherical particles are selected, uneven coverage of the emulsified composition can generally be further minimized. The size of the hydrophobic powder particles may be freely selected so that the mean particle diameter is about 2 nm to 30 μm for equivalent spherical particles. The particle diameter appropriate for enhancing the immediate whitening effect and wrinkle hiding effect varies according to the types of powders combined, but a diameter of about 5 nm to 10 μm is generally preferred.

The quantity of hydrophobic powder particles contained in the emulsified composition can be appropriately selected according to the specific form or application of the emulsified composition, the type of the powder particles, and other factors and is not particularly limited, but 0.01 to 20.0% by mass with respect to the composition is usually suitable, and 0.1 to 10.0% by mass is particularly suitable. The effects of including the powder particles in the emulsified composition tend to not be adequately demonstrated if the quantity is less than 0.01% by mass with respect to the composition, and if the quantity exceeds 20.0% by mass, a rough feel, runniness, stickiness, and other effects tend to occur in the emulsified composition due to excess admixture of the powder particles, and problems tend to occur in usability.

(b) Polyether-Modified Silicone (I)

The polyether-modified silicone (I) used in the emulsified composition is as described above, and more specifically:

at least one among $A^1$, $A^2$, and n number of $A^3$'s per molecule of the polyether-modified silicone (I) is the polyoxyalkylene group represented by the formula:

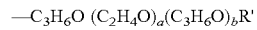

—$C_3H_6O$ $(C_2H_4O)_a(C_3H_6O)_b R'$ and the acyl groups expressed by R' include formyl, acetyl, propionyl, butyryl, acryloyl, benzoyl, toluoyl, and the like.

Furthermore, the alkyl groups with a carbon number of 1 to 4 expressed by R' include methyl, ethyl, i-propyl, n-propyl, t-butyl, and n-butyl groups, for example.

If the number of bonds a or b is less than 5, the stability over time of the emulsified composition obtained by adding the polyether-modified silicone is inadequate, and if the number of bonds is over 50, stickiness tends to easily occur in the emulsified composition.

The quantity of the polyoxyalkylene group contained in the polyether-modified silicone (I) is preferably 20 to 70% by mass (not including 20% by mass) with respect to the polyether-modified silicone (I). The stability over time of the emulsified composition that is obtained by including the polyether-modified silicone (I) is inadequate if the quantity of the polyoxyalkylene group contained therein is 20% by mass or less, and the compatibility in an oil phase of the emulsified composition tends to decrease if the quantity is more than 70% by mass.

The number of bonds m in the polyether-modified silicone (I) is also preferably an integer from 200 to 600, and n is preferably an integer from 1 to 40. If m is less than 200, or if n is zero, the stability over time of the emulsified composition obtained by adding the polyether-modified silicone (I) is inadequate, and if m is over 600, or if n is over 40, stickiness tends to occur in the emulsified composition.

The molecular weight of the polyether-modified silicone (I) is not particularly limited, and the viscosity thereof is also not particularly limited, but a suitable molecular weight is in the range of 45000 to 100000, particularly in the range of 50000 to 80000; and a suitable viscosity is in the range of 1000 to 100000 cst (at 25° C. or below) when the polyether-modified silicone (I) is in a solution of 50% by mass of octamethyl tetrasiloxane. This type of polyether-modified silicone is known as a gelling agent and is described, for example, in Japanese Laid-open Patent Application No. 5-311076.

The quantity of the polyether-modified silicone (I) contained in the emulsified composition is preferably 0.01 to 5.0% by mass with respect to the composition, and 0.05 to 3.0% by mass of the same is particularly suitable. It becomes difficult to impart adequate stability over time to the emulsified composition if the quantity of the polyether-modified silicone (I) contained therein is less than 0.01% by mass with respect to the composition, and if this quantity exceeds 5.0% by mass of the same, polymer-specific stickiness can occur in the emulsified composition and the emulsion performance can sometimes decrease.

(c) Ionic Water-Soluble Polymer Compound

The ionic water-soluble polymer compound is a water-soluble alkali-thickened polymer or water-soluble acid-thickened polymer that forms a gel by being neutralized by an alkaline agent or an acid agent. A water-soluble alkali-thickened polymer is suitable as the ionic water-soluble polymer compound used in the present invention. Specific examples include carboxyvinyl polymers, alkyl-modified carboxyvinyl polymers, acrylic acid/alkyl acrylate copolymers and the like, and salts of these polymers. One or more types of ionic water-soluble polymer compound can be included in the emulsified composition.

The alkaline agent or acid agent used to thicken the water-soluble alkali-thickened polymer or water-soluble acid-thickened polymer is not particularly limited. Sodium hydroxide, potassium hydroxide, ammonium hydroxide, triethanol amine, L-arginine, and other inorganic or organic bases can be cited as examples of the alkaline agent; and various organic acids or inorganic acids can be used as the acid agent.

The quantity of the ionic water-soluble polymer compound contained in the emulsified composition is preferably 0.01 to 2.0% by mass with respect to the composition, and particularly preferably 0.01 to 1.0% by mass thereof. It is difficult to obtain the desired thickening effects if the quantity of the ionic water-soluble polymer compound is less than 0.01% by mass with respect to the composition, and if the quantity thereof is more than 2.0% by mass, slipperiness or stickiness tends to be observed in the emulsified composition and the tactile evaluation thereof tends to decline. There is also a tendency for runniness to occur due to excess polymer during application.

(d) Silicone Oil

The dispersion properties and solubility of the polyether-modified silicone (I) can be enhanced, and stickiness can be further reduced, by including silicone oil in the emulsified composition.

The silicone oil is not particularly limited insofar as it is a silicone oil that can usually be used in cosmetics or other externally used compositions. Examples include methyl polysiloxane, methyl phenyl polysiloxane, octamethyl cyclotetrasiloxane, decamethyl cyclopentasiloxane, methyl polycyclosiloxane, methylhydrogen polysiloxane, dimethyl siloxane/methyl (POE) siloxane copolymer, dimethyl siloxane/methyl (POE) siloxane methyl (POP) siloxane copolymer, methyl polysiloxane emulsion, highly polymerized methyl polysiloxane, dimethyl siloxane/methyl (POP) siloxane copolymer, tetra decamethyl hexasiloxane, octamethyl trisiloxane, dodecamethyl cyclohexasiloxane, dimethyl siloxane/methylcetyloxysiloxane copolymer, and the like.

When silicone oil is included in the emulsified composition, the quantity of silicone oil included therein is preferably 0.1 to 50.0% by mass with respect to the composition, and particularly preferably 0.1 to 30% by mass thereof. It is difficult to identify the enhancement of solubility of the POE-modified silicone and pleasantness during use obtained by including silicone oil if the quantity of silicone oil contained therein is less than 0.1% by mass with respect to the composition, and if this quantity is more than 50.0% by mass, the emulsified composition takes on an oily feel, tends to lose its succulent feel, and sometimes fails to emulsify properly.

The method of manufacturing the emulsified composition is not particularly limited insofar as it is a method whereby an oil-in-water emulsified composition can ultimately be manufactured. The desired oil-in-water emulsified composition can usually be manufactured by adding hydrophobic powder particles, the polyether-modified silicone (I), and an oil phase preferably containing silicone oil to a water phase containing the ionic water-soluble polymer compound under stirring. It is also possible to manufacture the emulsified composition in a single step by emulsifying a mixture containing all of the added components. Another oil phase not containing hydrophobic powder particles (in the form of emulsified particles) may also be present in the emulsified composition.

It is possible for the water phase in the emulsified composition to be thickened by the ionic water-soluble polymer compound, and for the migration of eluted components and other ionic elements of the hydrophobic powder particles in the oil phase to the water phase to be minimized by the polyether-modified silicone (I). The effects of ionic elements on the thickened state of the ionic water-soluble polymer compound in the water phase can thereby be minimized, and the emulsified composition can be endowed with stability over time. Specifically, the effects originating from the hydrophobic powder and the succulent feel due to the thickening effect by the ionic water-soluble polymer compound can be provided in the emulsified composition while maintaining its stability over time.

As described above, the emulsified composition on a microscopic level is an oil-in-water emulsified composition in which hydrophobic powder particles and the polyether-modified silicone (I) are substantially contained in an oil phase that is an internal phase (when silicone oil is contained therein, the silicone oil is also included in the oil phase). The phrase "substantially contained in an oil phase" used herein means that the abovementioned components are contained in the oil phase with the degree of rigorousness at which the particles are approximated as remaining in the oil phase in the emulsified composition as a whole, and means not excluding cases in which the abovementioned components are identified as being present in the water phase in an externally used composition with such a degree that one skilled in the art considers range of error.

As described above, the emulsified composition is suitable for use as an externally used composition (composition for use on skin (including scalp and head hair)) that can be classified as a cosmetic, a drug, or a quasi drug. The form thereof is an oil-in-water emulsion, and when the composition is a cosmetic, milky lotions, creams, gels, mists, solid cosmetics, and the like can be cited as examples thereof. In the case of a drug or a quasi drug, ointments, creams, and the like can be cited as examples thereof.

When the emulsified composition is an externally used composition, other components that can be contained in an externally used composition may be included therein with such a degree that they do not critically hinder the effects of the present invention.

Examples include hydrophilic and hydrophobic powders other than the above exemplified powders, for which ion elution can be ignored, surfactants, humectants, medications, UV absorbers, preservatives, fragrances, and other agents. Whiteners, anti-chapping agents, and/or anti-wrinkle agents in particular are extremely well suited for inclusion therein as medications. Specifically, in a case in which the hydrophobic powder particles contained in the oil phase of the emulsified composition are a white powder (hydrophobized titanium oxide or the like, for example), the composition is extremely well suited as a whitening cosmetic when the ability to provide an immediate sense of whitening is considered. When the hydrophobic powder particles contained in the oil phase of the emulsified composition are spherical powder particles, long-term wrinkling or chapping relief can be obtained while at the same time providing an immediate wrinkle hiding effect or chapping relief.

Vitamin C, vitamin C derivatives (vitamin C phosphoric acid ester (salts), vitamin C 2-glucoside, and the like), arbutin, kojic acid, ellagic acid, Rucinol, resorcinol, and derivatives thereof can be cited as examples of whiteners.

β-Glycyrrhetic acid, glycyrrhizinic acid derivatives (VII), allantoin, azulene, hydrocortisone (VIII), and other anti-inflammatory agents; and tranexamic acid and other protease inhibiting agents can be cited as examples of anti-chapping agents.

Retinol, retinol palmitate, retinol acetate, and other retinoids; and glycolic acid, lactic acid, and other α-hydroxy acids can be cited as examples of anti-wrinkle agents.

The content of these components in the emulsified composition when whiteners, anti-chapping agents, and/or anti-wrinkle agents are used can be selected within the range in which the desired effects can be demonstrated according to the drug form, product type, specific type of medications used, and other attributes of the emulsified composition, and is not particularly limited.

Lotions, milky lotions, beauty lotions (essences), creams, massage cosmetics, sunscreen cosmetics, makeup base, foundations, lipsticks, rouge, eyeshadows, and the like can be cited as examples of product types when the emulsified composition is an externally used composition.

EXAMPLES

The present invention will be described in further detail hereinafter using examples, but the range of the present invention is not limited by these examples. Blend quantities in the present examples are expressed as percentages by mass unless otherwise indicated.

[Evaluation Methods]

Evaluation as to whether the test samples described hereinafter demonstrated the effects of the present invention was performed by the methods below.

(1) Stability over Time

The presence of (i) viscosity change and (ii) powder aggregation was verified immediately after preparation of a test sample and after long-term still standing storage (one month) at 50° C.

(i) Viscosity change was verified by measurement at 25° C. immediately after preparation of the sample and after the abovementioned still standing storage using a type-B viscometer (manufactured by Shibaura Systems Co., Ltd.). Evaluation was performed according to the criteria below based on the results.

A: Good (viscosity change is less than 50%)
B: Somewhat poor (viscosity change is less than 50 to 100%)
C: Poor (viscosity change is 100% or more)

(ii) The presence of powder aggregation was verified visually.

A: Absolutely no powder aggregation observed
B: Powder aggregation observed, although slight
C: Powder aggregation clearly observed (iii) A general evaluation of stability over time was performed based on the results of (i) and (ii).

A: Excellent stability over time ((i) and (ii) both A)
B: Somewhat poor stability over time ((i) and (ii) are both B, or either one of (i) or (ii) is A and the other is B)
C: Poor stability over time (when one of (i) and (ii) is C, stability over time is judged to be poor regardless of the evaluation given to the other)

(2) Practical Test

A sample (immediately after preparation and after one month) was applied to the faces of 40 female panelists immediately after the abovementioned stability over time was tested, and practical testing was performed for each of the following items: (i) succulent feel, (ii) absence of slipperiness, (iii) absence of stickiness, and (iv) absence of runniness.

For (i) succulent feel, evaluation was performed by calculating the ratio (%) of panelists who reported experiencing a succulent feel; (ii) absence of slipperiness was evaluated by calculating the ratio (%) of panelists who did not identify a slippery feel; (iii) absence of stickiness was evaluated by calculating the ratio (%) of panelists who did not report stickiness; and (iv) absence of runniness was evaluated by calculating the ratio (%) of panelists who did not report runniness.

(3) Evaluation of Skin Color Correcting Effects

When the practical test described in (2) above was performed, a specialist judge determined whether skin color had been improved for each panelist, and evaluation was performed by calculating the ratio (%) of panelists for whom it was determined that skin color had been improved.

(4) Evaluation of Ability to Accept and Hold Additional Makeup

Immediately after tests (2) and (3) were completed, a commercially available powdery foundation was further applied on places where the sample had been applied, and the ability immediately after applying the powdery foundation to (i) accept additional makeup and to (ii) hold additional makeup three hours after application were visually determined using a video microscope (manufactured by Keyence Corporation), and evaluation was performed for the ability to (i) accept additional makeup by calculating the ratio (%) of panelists for whom makeup acceptance was determined to be good, and evaluation of the ability to (ii) hold additional makeup was performed by calculating the ratio (%) of panelists for whom makeup hold was determined to be good.

[Sample Preparation]

Samples (essence: Working Examples 1 through 5; Comparative Examples 1 through 7) were prepared according to the formulae shown in Table 1 (working examples) and Table 2 (comparative examples). Preparation was performed by adding a uniform dispersion of a mixture of components 9 through 18 to a solution in which ingredients 1 through 8 and 19 through 23 were mixed and dissolved, and dispersing the product using a stirring machine. The hydrophobic powder particles were a powder obtained by performing the alkyl-modified silicone treatment (tetradecene was added after bringing powder particles into contact with 1,3,5,7-tetramethyl cyclotetrasiloxane) by the usual method, and the term "unprocessed" refers to powder (hydrophilic) that has not been hydrophobized.

The polyether-modified silicone 1 is a low-molecular weight (MW about 6000) dimethyl polysiloxane/methyl (polyoxyethylene) siloxane copolymer in which R, $A^1$, and $A^2$ in the polyether-modified silicone (I) described above are methyl groups, $A^3$ is a methyl group or the polyoxyalkylene group R' (the polyether content thereof is approximately 20% by mass); and in the polyoxyalkylene group R', m is 50 to 60, n is 3, a is 0, and b is 9.

The polyether-modified silicone 2 is a high-molecular-weight (MW about 55000) poly(oxyethylene/oxypropylene) methyl polysiloxane copolymer in which R, $A^1$, and $A^2$ in the polyether-modified silicone (I) are methyl groups, $A^3$ is a methyl group or the polyoxyalkylene group R' (the polyether content thereof is approximately 45% by mass); and in the polyoxyalkylene group R', m is 400, n is 10, a is 24, and b is 24.

The blend quantities in the tables are in % by mass with respect to the entire quantity of the sample, and the symbol "—" indicates that the component was not admixed into the sample (0% by mass).

TABLE 1

| Ingredient | Blend Quantity (% by mass) Working Example No. | | | | |
|---|---|---|---|---|---|
| | 1 | 2 | 3 | 4 | 5 |
| 1. Acrylic acid/alkyl acrylate copolymer | 0.1 | — | — | 0.05 | — |
| 2. Carboxyvinyl polymer | 0.1 | 0.2 | 0.01 | 0.15 | 0.05 |
| 3. Xanthan gum | — | — | — | — | — |
| 4. Hydroxyethyl cellulose | — | — | — | 0.1 | — |
| 5. Agar | — | — | — | — | — |
| 6. Butylene glycol | 5.0 | 5.0 | 5.0 | 5.0 | 5.0 |
| 7. Glycerin | 15.0 | 3.0 | 10.0 | — | 3.0 |
| 8. Ethanol | 5.0 | 10.0 | — | 4.0 | 10.0 |
| 9. Unprocessed titanium oxide powder | — | — | — | — | — |

TABLE 1-continued

| Ingredient | Blend Quantity (% by mass) Working Example No. | | | | |
|---|---|---|---|---|---|
| | 1 | 2 | 3 | 4 | 5 |
| 10. Unprocessed iron oxide powder | — | — | — | — | — |
| 11. Unprocessed titanated mica pigment | — | — | — | — | — |
| 12. Hydrophobized titanium oxide powder | — | 1.0 | 0.5 | 2.0 | 8.0 |
| 13. Hydrophobized iron oxide powder | — | — | — | 0.2 | 2.0 |
| 14. Hydrophobized titanated mica pigment | 1.5 | — | 0.5 | — | — |
| 15. Methyl polysiloxane | 5.0 | 10.0 | 2.0 | 5.0 | 30.0 |
| 16. Octamethyl cyclotetrasiloxane | 5.0 | — | 8.0 | 5.0 | — |
| 17. Polyether-modified silicone 1 | — | — | — | — | — |
| 18. Polyether-modified silicone 2 | 2.0 | 0.5 | 3.0 | 1.0 | 0.05 |
| 19. POE hydrogenated castor oil | — | 1.0 | 0.5 | — | — |
| 20. Potassium hydroxide (1% aqueous solution) | 8.0 | 8.0 | 2.0 | 8.0 | 8.0 |
| 21. Antioxidant | Suitable amount | Suitable amount | Suitable amount | Suitable amount | Suitable amount |
| 22. Preservative | Suitable amount | Suitable amount | Suitable amount | Suitable amount | Suitable amount |
| 23. Purified water | Balance | Balance | Balance | Balance | Balance |

TABLE 2

| Ingredient | Blend Quantity (% by mass) Comparative Example No. | | | | | | |
|---|---|---|---|---|---|---|---|
| | 1 | 2 | 3 | 4 | 5 | 6 | 7 |
| 1. Acrylic acid/alkyl acrylate copolymer | 0.1 | — | — | — | — | 0.05 | — |
| 2. Carboxyvinyl polymer | 0.1 | 0.2 | 0.05 | — | — | 0.15 | — |
| 3. Xanthan gum | — | — | — | 1.5 | — | — | — |
| 4. Hydroxyethyl cellulose | — | — | — | — | 2.0 | 0.1 | — |
| 5. Agar | — | — | — | — | — | — | 3.0 |
| 6. Butylene glycol | 5.0 | 5.0 | 5.0 | 5.0 | 5.0 | 5.0 | 5.0 |
| 7. Glycerin | 15.0 | 3.0 | 10.0 | 3.0 | 15.0 | — | 0.5 |
| 8. Ethanol | 5.0 | 10.0 | — | 10.0 | 7.0 | 4.0 | 3.0 |
| 9. Unprocessed titanium oxide powder | — | 1.0 | — | — | — | — | — |
| 10. Unprocessed iron oxide powder | — | 0.2 | — | — | — | — | — |
| 11. Unprocessed titanated mica pigment | — | 0.5 | — | — | — | — | — |
| 12. Hydrophobized titanium oxide powder | — | — | 0.5 | 1.0 | 1.0 | 2.0 | 1.0 |
| 13. Hydrophobized iron oxide powder | — | — | — | — | — | 0.2 | — |
| 14. Hydrophobized titanated mica pigment | — | — | 0.5 | — | — | — | — |
| 15. Methyl polysiloxane | 5.0 | 10.0 | 2.0 | 10.0 | 10.0 | 5.0 | 10.0 |
| 16. Octamethyl cyclotetrasiloxane | 5.0 | — | 8.0 | 8.0 | 20.0 | 5.0 | 1.0 |
| 17. Polyether-modified silicone 1 | — | — | — | — | — | 1.0 | — |
| 18. Polyether-modified silicone 2 | 2.0 | 0.5 | — | 1.0 | 1.0 | — | 1.0 |
| 19. POE hydrogenated castor oil | — | 1.0 | 0.5 | 1.0 | — | — | — |
| 20. Potassium hydroxide (1% aqueous solution) | 8.0 | 8.0 | 2.0 | — | — | 8.0 | 8.0 |

TABLE 2-continued

| Ingredient | Blend Quantity (% by mass) Comparative Example No. | | | | | | |
|---|---|---|---|---|---|---|---|
| | 1 | 2 | 3 | 4 | 5 | 6 | 7 |
| 21. Antioxidant | Suitable amount | Suitable amount | Suitable amount | Suitable amount | Suitable amount | Suitable amount | Suitable amount |
| 22. Preservative | Suitable amount | Suitable amount | Suitable amount | Suitable amount | Suitable amount | Suitable amount | Suitable amount |
| 23. Purified water | Balance | Balance | Balance | Balance | Balance | Balance | Balance |

[Test Results]

The results obtained for the samples (essence: Working Examples 1 through 5 and Comparative Examples 1 through 7) obtained using the ingredients above are shown in Table 3.

TABLE 3

| | Working Example No. | | | | | Comparative Example No. | | | | | | |
|---|---|---|---|---|---|---|---|---|---|---|---|---|
| | 1 | 2 | 3 | 4 | 5 | 1 | 2 | 3 | 4 | 5 | 6 | 7 |
| (1) Stability over time | A | A | A | A | A | A | C | C | B | B | C | B |
| (2) Practical test | | | | | | | | | | | | |
| (i) Succulent feel | 70 | 67.5 | 92.5 | 67.5 | 75 | 70 | 70 | 90 | 22.5 | 20 | 67.5 | 47.5 |
| (ii) Absence of slipperiness | 77.5 | 80 | 87.5 | 57.5 | 90 | 75 | 77.5 | 87.5 | 7.5 | 12.5 | 72.5 | 60 |
| (iii) Absence of stickiness | 65 | 77.5 | 75 | 70 | 72.5 | 62.5 | 75 | 80 | 22.5 | 12.5 | 77.5 | 60 |
| (iv) Absence of runniness | 100 | 100 | 100 | 97.5 | 95 | 100 | 100 | 97.5 | 37.5 | 10 | 100 | 20 |
| (3) Skin color correcting effects | 52.5 | 67.5 | 55 | 67.5 | 75 | 0 | 37.5 | 55 | 62.5 | 60 | 65 | 57.5 |
| (4) Makeup acceptance and hold | | | | | | | | | | | | |
| (i) Makeup acceptance | 60 | 57.5 | 65 | 65 | 67.5 | 35 | 37.5 | 62.5 | 40 | 22.5 | 65 | 62.5 |
| (ii) Makeup hold | 72.5 | 60 | 67.5 | 75 | 62.5 | 15 | 27.5 | 65 | 37.5 | 20 | 65 | 47.5 |

According to the results obtained above, particularly when the blend quantities of the essential ingredients were in the preferable range, the results of the practical test of succulent feel and other effects were good with maintaining the stability over time, and the results of evaluating the skin color correcting effects, which are mainly dependent on the powder particles, were also good. The makeup acceptance and makeup hold were also good in cases in which the product was used as a makeup foundation. In contrast, Comparative Example 1 in which the powder particles were not admixed, had obviously poor skin color correcting effects, which are dependent on the powder particles, and the makeup acceptance or makeup hold was also poor when the product was used as a makeup foundation. Although some skin color correcting effect was obtained in Comparative Example 2 in which the powder particles were hydrophilic, stability thereof over time was inferior. The stability over time was inferior in Comparative Example 3, in which the polyether-modified silicone was not admixed. Comparative Examples 4 and 5, in which xanthan gum, hydroxyethyl cellulose, and other thickening agents were admixed instead of the ionic water-soluble polymer compound, had poor evaluations in the practical test. Problems in stability over time were also identified in Comparative Example 6, in which the polyether-modified silicone 1 was used, the number of bonds m of the polyether-modified silicone (I) being smaller than the preferable range. Comparative Example 7, in which agar was used without admixing an ionic polymer therein, had somewhat poor stability over time, runniness was identified therein, and the makeup acceptance thereof was inferior.

Examples of formulations of the emulsified composition will be described as working examples hereinafter. The emulsified compositions in these working examples remained stable over time and had good evaluations in the practical tests and good evaluations of effects that are dependent on the action of the hydrophobic powder. The hydrophobized powder in the working examples below is a powder obtained by performing alkyl-modified silicone treatment according to the usual method.

[Working Example 6] Milky Lotion

| Ingredients | Blend Quantity (% by mass) |
|---|---|
| 1. Acrylic acid/alkyl acrylate copolymer | 0.08 |
| 2. Carboxyvinyl polymer | 0.5 |
| 3. Xanthan gum | 0.3 |
| 4. Squalane | 1.0 |
| 5. Decamethyl pentasiloxane | 10.0 |
| 6. Methyl polysiloxane | 1.5 |
| 7. Polyether-modified silicone 2 | 1.0 |
| 8. Hydrophobized titanium oxide powder (particle diameter: 200 to 400 nm) | 0.8 |
| 9. Octyl methoxy cinnamate | 1.0 |
| 10. Glycerin | 5.0 |
| 11. 1,3-butylene glycol | 8.0 |
| 12. Ascorbic acid 2-glucoside | 5.0 |
| 13. Aqueous solution (1%) of sodium hydroxide | 10.0 |
| 14. Ethanol | 2.0 |
| 15. Antioxidant | Suitable Amount |
| 16. Preservative | Suitable Amount |
| 17. Purified water | Balance |

<Manufacturing Method>

An emulsion was obtained by a process whereby a mixture in which components 4 through 9 had been uniformly dispersed was added to a mixture in which components 1 through 3 and 10 through 17 had been mixed and dissolved, and the product was stirred to obtain a uniform dispersion.

[Working Example 7] Cream

| Ingredients | Blend Quantity (% by mass) |
| --- | --- |
| 1. Carboxyvinyl polymer | 0.8 |
| 2. Stearyl alcohol | 1.0 |
| 3. Solid paraffin | 1.0 |
| 4. Petrolatum | 1.0 |
| 5. Methylphenyl polysiloxane | 3.0 |
| 6. Polyether-modified silicone 2 | 3.0 |
| 7. Hydrophobized titanium oxide powder (particle diameter: 200 to 400 nm) | 5.0 |
| 8. Jojoba oil | 2.0 |
| 9. Pentaerythrityl tetraoctanoate | 5.0 |
| 10. POE (25) cetyl alcohol ether | 1.0 |
| 11. Glycerin monostearate | 0.8 |
| 12. Glycerin | 3.0 |
| 13. 1,3-Butylene glycol | 3.0 |
| 14. Retinol acetate | 0.2 |
| 15. Dextrin | 1.2 |
| 16. Aqueous solution (1%) of sodium hydroxide | 2.0 |
| 17. Ethanol | 10.0 |
| 18. Edetate trisodium | 0.1 |
| 19. Preservative | Suitable Amount |
| 20. Purified water | Balance |

<Manufacturing Method>

A cream was obtained by a process whereby a heated mixture of components 2 through 4, 8 through 11, and 14 and 15, and a mixture of components 5 through 7 were added to a mixture of components 1, 12, 13, and 16 through 20, and the product was stirred, mixed, and cooled.

[Working Example 8] Gel

| Ingredients | Blend Quantity (% by mass) |
| --- | --- |
| 1. Acrylic acid/alkyl acrylate copolymer | 0.1 |
| 2. Carboxyvinyl polymer | 0.1 |
| 3. Octamethyl cyclotetrasiloxane | 8.0 |
| 4. Dimethicone/vinyldimethicone cross-polymer | 2.0 |
| 5. Polyether-modified silicone 2 | 2.0 |
| 6. Hydrophobized titanium oxide powder (particle diameter: 200 to 400 nm) | 0.3 |
| 7. Glycerin | 2.0 |
| 8. 1,3-Butylene glycol | 5.0 |
| 9. Arbutin | 5.0 |
| 10. Aqueous solution (1%) of sodium hydroxide | 3.0 |
| 11. Buffering agent | Suitable Amount |
| 12. Preservative | Suitable Amount |
| 13. Purified water | Balance |

<Manufacturing Method>

A mixture in which components 3 through 6 had been uniformly dispersed was added to a mixture in which components 1, 2, and 7 through 13 had been mixed and dissolved, the product was stirred and uniformly dispersed, and a gel was obtained.

[Working Example 9] Sunscreen Cosmetic

| Ingredients | Blend Quantity (% by mass) |
| --- | --- |
| 1. Carboxyvinyl polymer | 0.2 |
| 2. Xanthan gum | 0.1 |
| 3. Octamethyl cyclotetrasiloxane | 20.0 |
| 4. Dimethyl silicone | 7.0 |
| 5. Phenylmethyl silicone | 2.0 |
| 6. Polyether-modified silicone 2 | 2.0 |
| 7. Hydrophobized titanium oxide powder (particle diameter: 10 to 50 nm) | 5.0 |
| 8. Hydrophobized zinc oxide powder | 5.0 |
| 9. Octyl methoxy cinnamate | 5.0 |
| 10. Butyl methoxybenzoyl methane | 2.0 |
| 11. Polyoxyethylene (60) hydrogenated castor oil | 1.0 |
| 12. 1,3-Butylene glycol | 6.0 |
| 13. Dipotassium glycyrrhizate | 1.0 |
| 14. Silicic anhydride | 2.0 |
| 15. Aqueous solution (1%) of sodium hydroxide | 1.0 |
| 16. Ethanol | 10.0 |
| 17. Preservative | Suitable Amount |
| 18. Purified water | Balance |

<Manufacturing Method>

A mixture in which components 3 through 10 had been uniformly dispersed was added to a mixture in which components 1, 2, and 11 through 18 had been mixed and dissolved, the product was stirred and uniformly dispersed, and a sunscreen cosmetic was obtained.

[Working Example 10] Makeup Base

| Ingredients | Blend Quantity (% by mass) |
| --- | --- |
| 1. Carboxyvinyl polymer | 0.2 |
| 2. Hydroxypropyl cellulose | 0.1 |
| 3. Octamethyl cyclotetrasiloxane | 6.0 |
| 4. Dimethyl silicone | 6.0 |
| 5. Trictanoin | 3.0 |
| 6. Mineral oil | 2.0 |
| 7. Polyether-modified silicone 2 | 2.0 |
| 8. Hydrophobized titanium oxide powder (particle diameter: 10 to 50 nm) | 1.5 |
| 9. Hydrophobized iron oxide powder | 0.1 |
| 10. 1,3-Butylene glycol | 6.0 |
| 11. Aqueous solution (1%) of sodium hydroxide | 20.0 |
| 12. Ethanol | 6.0 |
| 13. Preservative | Suitable Amount |
| 14. Purified water | Balance |

<Manufacturing Method>

A mixture in which components 3 through 9 had been uniformly dispersed was added to a mixture in which components 1, 2, and 10 through 14 had been mixed and dissolved, the product was stirred and uniformly dispersed, and a makeup base was obtained.

[Working Example 11] Liquid Foundation

| Ingredients | Blend Quantity (% by mass) |
| --- | --- |
| 1. Carboxyvinyl polymer | 0.1 |
| 2. Stearyl alcohol | 1.0 |
| 3. Cetyl octanoate | 5.0 |
| 4. Stearic acid | 0.8 |
| 5. Methyl polysiloxane | 5.0 |
| 6. Octamethyl cyclotetrasiloxane | 2.0 |

-continued

| | Ingredients | Blend Quantity (% by mass) |
|---|---|---|
| 7. | Polyether-modified silicone 2 | 4.0 |
| 8. | Hydrophobized titanium oxide powder (particle diameter: 200 to 400 nm) | 4.0 |
| 9. | Hydrophobized iron oxide powder | 0.5 |
| 10. | 1,3-Butylene glycol | 6.0 |
| 11. | POE alkyl ether | 1.0 |
| 12. | Aqueous solution (1%) of sodium hydroxide | 3.0 |
| 13. | Ethanol | 6.0 |
| 14. | Preservative | Suitable Amount |
| 15. | Purified water | Balance |

<Manufacturing Method>

A mixture in which components 2 through 9 had been uniformly dispersed was added to a mixture in which components 1 and 10 through 15 had been mixed and dissolved, the product was stirred and uniformly dispersed, and a liquid foundation was obtained. [Working Example 12] Two-Layer Lotion

| | Ingredients | Blend Quantity (% by mass) |
|---|---|---|
| 1. | Carboxyvinyl polymer | 0.01 |
| 2. | Sodium polyacrylate | 0.01 |
| 3. | Dimethyl silicone | 0.8 |
| 4. | Polyether-modified silicone 2 | 0.03 |
| 5. | Hydrophobized titanium oxide powder (particle diameter: 200 to 400 nm) | 0.3 |
| 6. | Polymethyl methacrylate powder (PMMA powder) | 2.0 |
| 7. | PEG/PPG copolymer | 0.5 |
| 8. | Dipropylene glycol | 7.0 |
| 9. | Tranexamic acid | 3.0 |
| 10. | Ethanol | 8.0 |
| 11. | Preservative | Suitable Amount |
| 12. | Purified water | Balance |

<Manufacturing Method>

A mixture in which components 3 through 6 had been uniformly dispersed was added to a mixture in which components 1, 2, and 7 through 12 had been mixed and dissolved, the product was stirred and uniformly dispersed, and a two-layer lotion was obtained.

[Working Example 13] Beauty Lotion

| | Ingredients | Blend Quantity (% by mass) |
|---|---|---|
| 1. | Carboxyvinyl polymer | 0.3 |
| 2. | Acrylic acid/alkyl acrylate copolymer | 0.1 |
| 3. | Succinoglucan | 0.3 |
| 4. | Hydroxypropyl methylcellulose | 0.1 |
| 5. | Pentaerythrityl tetraoctanoate | 3.0 |
| 6. | Dioctyl succinate | 3.0 |
| 7. | Octamethyl cyclotetrasiloxane | 2.0 |
| 8. | Decamethyl cyclopentasiloxane | 2.0 |
| 9. | Dodecamethyl cyclohexasiloxane | 1.0 |
| 10. | Methyl polysiloxane | 1.0 |
| 11. | Polyether-modified silicone 2 | 1.5 |
| 12. | Hydrophobized titanium oxide powder (particle diameter: 200 to 400 nm) | 1.0 |
| 13. | Hydrophobized titanated mica powder | 0.5 |
| 14. | 1,3-Butylene glycol | 10.0 |
| 15. | Glycerin | 1.0 |
| 16. | PEG/PPG copolymer | 1.0 |
| 17. | Ascorbic acid 2-glucoside | 3.0 |

-continued

| | Ingredients | Blend Quantity (% by mass) |
|---|---|---|
| 18. | Aqueous solution (1%) of sodium hydroxide | 6.0 |
| 19. | Ethanol | 5.0 |
| 20. | Antioxidant | Suitable Amount |
| 21. | Preservative | Suitable Amount |
| 22. | Purified water | Balance |

<Manufacturing Method>

A mixture of components 5 and 6 and a mixture in which components 7 through 13 had been uniformly dispersed/mixed were added to a mixture in which components 1 through 4 and 14 through 22 had been mixed and dissolved, the product was stirred and uniformly dispersed, and a beauty lotion was obtained.

[Working Example 14] Milky Lotion

| | Ingredients | Blend Quantity (% by mass) |
|---|---|---|
| 1. | Carboxyvinyl polymer | 0.2 |
| 2. | Acrylic acid/alkyl acrylate copolymer | 0.05 |
| 3. | Hydroxypropyl cellulose | 0.1 |
| 4. | Cellulose gum | 0.1 |
| 5. | Octamethyl cyclotetrasiloxane | 2.0 |
| 6. | Decamethyl cyclopentasiloxane | 2.0 |
| 7. | Dodecamethyl cyclohexasiloxane | 1.0 |
| 8. | Methyl polysiloxane | 1.0 |
| 9. | Polyether-modified silicone 2 | 1.5 |
| 10. | Hydrophobized titanium oxide powder (particle diameter: 200 to 400 nm) | 1.0 |
| 11. | Hydrophobized titanated mica powder | 0.5 |
| 12. | 1,3-Butylene glycol | 10.0 |
| 13. | Glycerin | 1.0 |
| 14. | PEG/PPG copolymer | 1.0 |
| 15. | PEG/PPG dimethyl ether | 1.0 |
| 16. | PEG/PPG cetyl ether | 0.5 |
| 17. | Arbutin | 4.0 |
| 18. | Aqueous solution (1%) of sodium hydroxide | 0.7 |
| 19. | Ethanol | 5.0 |
| 20. | Stabilizer | Suitable Amount |
| 21. | Antioxidant | Suitable Amount |
| 22. | Preservative | Suitable Amount |
| 23. | Purified water | Balance |

<Manufacturing Method>

A mixture in which components 5 through 11 had been uniformly dispersed/mixed was added to a mixture in which components 1 through 4 and 12 through 23 had been mixed and dissolved, the product was stirred and uniformly dispersed, and a milky lotion was obtained.

INDUSTRIAL APPLICABILITY

By the present invention, an oil-in-water emulsified composition containing hydrophobic powder particles is provided, whereby a succulent feel originating from thickening effect caused by an ionic water-soluble polymer compound and effects originating from the hydrophobic powder particles can be demonstrated stably over time.

The invention claimed is:

1. An oil-in-water emulsified composition comprising:
   (a) hydrophobic powder particles;
   (b) a polyether-modified silicone represented by the following formula (I):

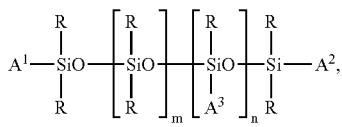

in which $A^1$, $A^2$, and n number of $A^3$'s are the same or different, and are a methyl group, a phenyl group, or a polyoxyalkylene group represented by the general formula:

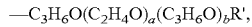

wherein R' is a hydrogen atom, an acyl group, or an alkyl group with a carbon number of 1 to 4; and a and b are the same or different integers from 5 to 50; and at least one among n number of $A^3$'s per molecule of the polyether-modified silicone (I) is the polyoxyalkylene group;

R is a methyl group or a phenyl group;

m is an integer from 200 to 600; and n is an integer from 1 to 40; and (c) an ionic water-soluble polymer compound which is selected from the group consisting of a carboxyvinyl polymer, an alkyl-modified carboxyvinyl polymer, and an acrylic acid/alkyl acrylate copolymer.

2. The oil-in-water emulsified composition according to claim 1, wherein the hydrophobic powder particles and the polyether-modified silicone (I) are substantially contained in the oil phase.

3. The oil-in-water emulsified composition according to claim 1, wherein the hydrophobic powder particles are one or more types of hydrophobized powder particles of materials selected from the group consisting of titanium oxide, iron oxide, magnesium oxide, zinc oxide, calcium oxide, calcium phosphate, calcium carbonate, alumina, aluminum hydroxide, barium sulfate, an iridescent pigment, talc, and composite powders obtained using these materials.

4. The oil-in-water emulsified composition according to claim 1, comprising 0.01 to 20.0% by mass of hydrophobic powder particles, 0.01 to 5.0% by mass of polyether-modified silicone (I), and 0.01 to 2.0% by mass of the ionic water-soluble polymer compound with respect to the composition.

5. The oil-in-water emulsified composition according to claim 1, containing a skin whitening agent, an anti-chapping agent, and/or an anti-wrinkle agent.

6. The oil-in-water emulsified composition according to claim 1, wherein the oil-in-water emulsified composition is an externally used composition.

7. The oil-in-water emulsified composition according to claim 1, further comprising (d) silicone oil.

8. The oil-in-water emulsified composition according to claim 7, wherein the hydrophobic powder particles, the polyether-modified silicone (I), and the silicone oil are substantially contained in the oil phase.

9. The oil-in-water emulsified composition according to claim 7, comprising 0.01 to 20.0% by mass of hydrophobic powder particles, 0.01 to 5.0% by mass of polyether-modified silicone (I), 0.01 to 2.0% by mass of the ionic water-soluble polymer compound, and 0.1 to 50.0% by mass of silicone oil with respect to the composition.

* * * * *